United States Patent [19]
Genco et al.

[11] Patent Number: 5,455,041
[45] Date of Patent: Oct. 3, 1995

[54] METHOD FOR INDUCING PERIODONTAL TISSUE REGENERATION

[75] Inventors: Robert J. Genco, Buffalo; Moon-Il Cho, Amherst, both of N.Y.

[73] Assignee: Research Foundation of State University of New York at Buffalo, Buffalo, N.Y.

[21] Appl. No.: 121,041

[22] Filed: Sep. 13, 1993

[51] Int. Cl.⁶ ............................ A61K 9/48; A61K 9/14; A61C 5/02
[52] U.S. Cl. ............... 424/435; 424/451; 424/489; 514/965; 433/215
[58] Field of Search .................... 424/435, 451, 424/489; 514/965; 433/215

[56] References Cited

U.S. PATENT DOCUMENTS

| | | | |
|---|---|---|---|
| 4,702,734 | 10/1987 | Terranova et al. | 604/54 |
| 4,961,707 | 10/1990 | Magnusson et al. | 433/215 |
| 5,019,559 | 5/1991 | Antoniades et al. | 514/21 |
| 5,059,123 | 10/1991 | Jernberg | 433/215 |
| 5,077,049 | 12/1991 | Dunn et al. | 424/426 |
| 5,093,179 | 3/1992 | Scantlebury et al. | 428/158 |
| 5,124,316 | 6/1992 | Antoniades et al. | 514/12 |
| 5,128,321 | 7/1992 | Murray et al. | 514/12 |
| 5,129,824 | 7/1992 | Keller | 433/215 |
| 5,149,691 | 9/1992 | Rutherford | 514/12 |
| 5,197,882 | 3/1993 | Jernberg | 433/215 |

*Primary Examiner*—Thurman K. Page
*Assistant Examiner*—Carlos Azpuru
*Attorney, Agent, or Firm*—Hodgson, Russ, Andrews, Woods & Goodyear

[57] ABSTRACT

A method for inducing periodontal regeneration including soft tissue, cementum, and bone regeneration, resulting in a type of healing characteristic of the anatomy and architecture of the undiseased tissue, comprising treating the surface of the damaged root with a demineralizing agent, and then applying a growth factor directly to the treated bone surface.

11 Claims, 8 Drawing Sheets

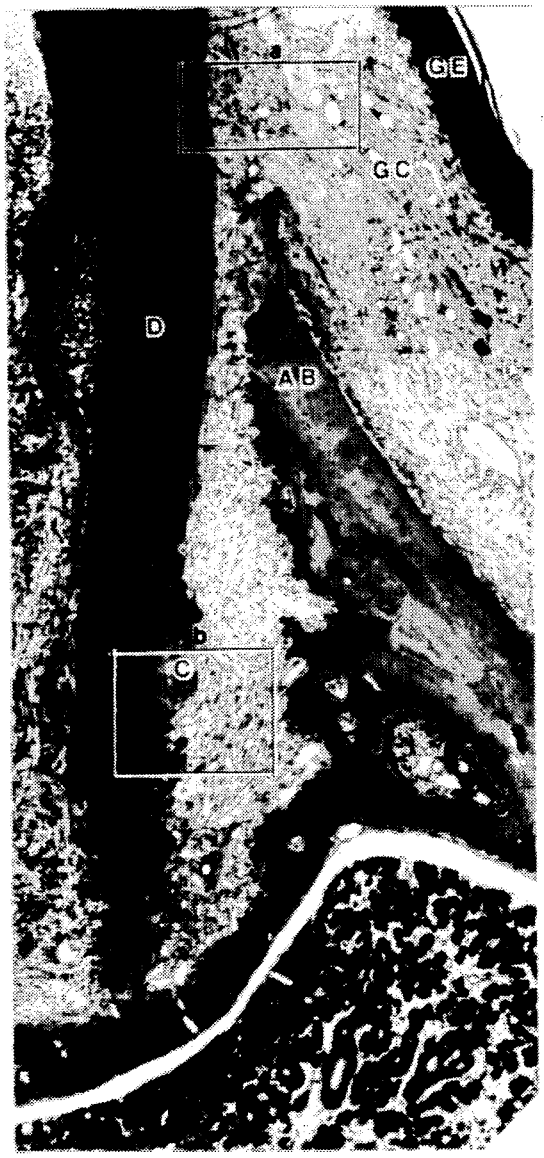
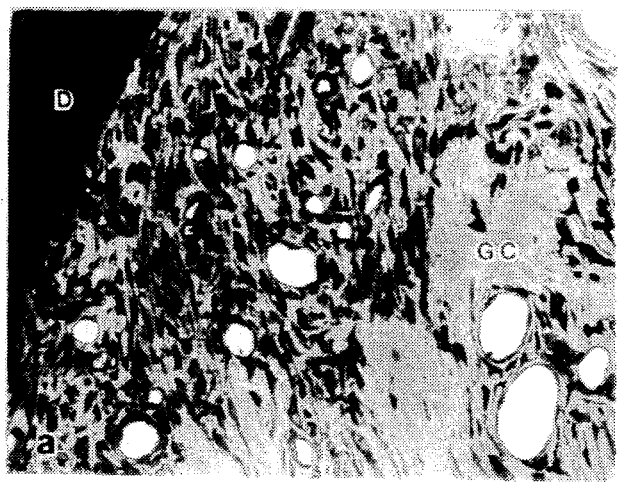
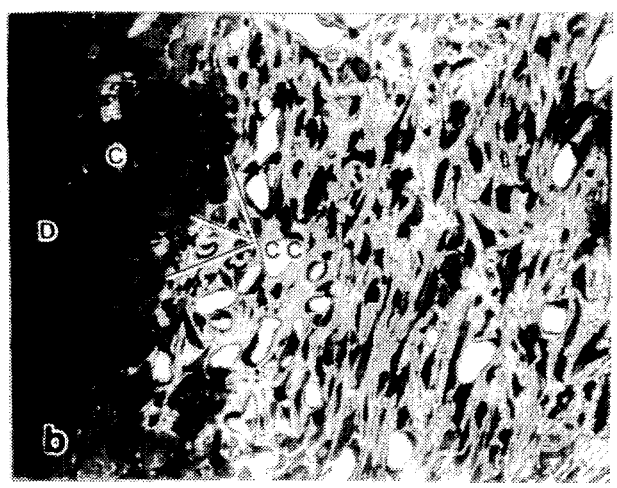
FIG. 3
FIG. 3a
FIG. 3b

METHOD FOR INDUCING PERIODONTAL TISSUE REGENERATION

FIELD OF THE INVENTION

The present invention relates to a novel method for the regeneration of tooth supporting tissues pathologically altered by disease such as periodontal disease. More particularly, the present invention provides a method which induces an orderly cascade of cell migration, proliferation, and differentiation resulting in a type of healing characteristic of the original architecture and normal anatomy of the periodontium.

BACKGROUND OF THE INVENTION

The tooth supporting tissues affected by periodontal disease include the gingival tissue (gums); periodontal ligament (connective tissue located between the cementum and alveolar bone); cementum (mineralized connective tissue covering the root surface of a tooth); and the alveolar bone (the bone socket). Depending on the progression of the disease, there may occur a destruction of the periodontal ligament (PDL), alveolar bone loss, and apical migration of the junctional epithelium. Advanced periodontal disease may result in the formation of periodontal pockets harboring bacterial plaque, loss of tooth supporting tissues and progressive loosening and eventual loss of teeth.

Current periodontal therapies are directed at arresting the progression of the pathological alterations due to periodontal disease, as well as promoting the repair or regeneration of the periodontal wounds. Such therapies include wound and bone regeneration using purified growth factors (See for example, Antonaides et al. U.S. Pat. Nos. 4,861,757, 5,019,559, and 5,124,316); using growth factors in combination with dexamethasone to enhance the mitogenic effect of the growth factor (Rutherford, U.S. Pat. No. 5,149,691); using root surface demineralization (Terranova et al., U.S. Pat. No. 4,702,734; for an excellent review see Lowenguth and Blieden, 1993, *Periodontology* 2000, 1:54–68); and the use of periodontal barriers such as membranes (Magnuson et al., U.S. Pat. No. 4,961,707), microparticles (Jernberg, U.S. Pat. Nos. 5,059,123 and 5,197,882), biodegradable polymers (Dunn et al., U.S. Pat. No. 5,077,049) and biocompatible porous material comprising expanded polytetrafluoroethylene (Scantlebury et al., U.S. Pat. No. 5,093,179).

Growth factors, particularly platelet-derived growth factors (PDGF) and insulin-like growth factor (IGF-1) are known to stimulate mitogenic, chemotactic and proliferative (differentiation) cellular responses. Root surface demineralization is known to enhance the binding of fibronectin and fibroblasts to the root surface. Periodontal barriers are used to exclude contact between the root surfaces and the gingival epithelium and connective tissue thereby creating a space to allow the entry of periodontal ligament (PDL) cells to colonize the root surfaces preferentially over gingival epithelial cells, gingival fibroblasts, or osteoblasts. Periodontal barriers have been designed so that they may also be used for the controlled delivery of chemotherapeutic agents such as tissue regenerative agents (i.e. growth factors), antibiotics, and anti-inflammatory agents to promote periodontal healing and regeneration.

Several major aberrations have been observed and recognized as the major causes for the failure of current periodontal regenerative therapies. These include downgrowth of the junctional epithelium, failure to establish reattachment of newly formed PDL collagen fibers to the root surface, root resorption, ankylosis of the root to the surrounding alveolar process, and incomplete PDL regeneration. Ankylosis (See for example Antonaides et al., supra, and Magnuson et al., supra) occurs when periodontal regeneration does not occur in an orderly manner, i.e. bone cells reach the root surface where an imperfect and dysfunctional fusion occurs rather than bone cells being anchored to the root surface via a connective tissue attachment (cementum, and collagen ligament formation) as in original periodontium. Also, slow and/or improper repair of the PDL is associated with ankylosis between the roots unprotected by cementum and PDL and the corresponding alveolar bone (Wikesjo et al. 1988, *J. Clin. Periodontol.* 15:73–80). With current therapies, regeneration of soft tissue and bone in the healed wounds does not result in tissue with the anatomy, architecture, and thus function, characteristic of the original periodontium. In addition, none of the current therapies disclose predictable healing in periodontal disease of Class III furcation lesions which are "through-and-through", i.e. no bone in the lesion to begin with. (Pontoriero et al., 1989, *J. Clin. Periodontol.* 16:170–174).

SUMMARY AND OBJECTS OF THE INVENTION

An object of the present invention is to provide a comprehensive method for periodontal regenerative therapy, i.e. growth factor-modulated guided tissue regenerative therapy, which effectively restores the normal anatomy of the periodontium.

Another object of the present invention is to provide a method which induces a cascade of cell migration and differentiation resulting in a type of healing characteristic of the original architecture of the periodontium.

A further object of the present invention is to provide a method of regenerative therapy useful for the healing of Class III furcation lesions in periodontal disease, and also with applications in regenerating soft tissue and bone in similar lesions from different anatomical sites.

The present invention, in one embodiment, provides a method for a simple and direct periodontal regenerative therapy comprising: (a) treatment of a root surface in a periodontal wound with a decalcifying agent, thus preparing the root surface for application of growth factor; (b) applying the growth factor directly to the treated root surface; and (c) positioning a periodontal barrier between the gingival tissue and the root, and closing of the wound.

BRIEF DESCRIPTION OF THE FIGURES

The abbreviations used in the figures areas follows: AB: Alveolar bone; BV: Blood vessel; C: Cementum; CC: Cementoclast; CMSC: Cellular mixed stratified cementum; D: Dentin; DC: Dentinoclast; DEJ: Dentinoenamel junction; DT: Dentinal tubule; GE: Gingival epithelium; GC: Gingival connective tissue; JE: Junctional epithelium; N: Nerve; PDL: Periodontal ligament

FIG. 3 represents a photomicrograph showing periodontal regeneration 6 days after reimplantation of a demineralized molar.

FIG. 3a is an enlargement of portion a of FIG. 3 showing improved healing in the apical wound area, and complete healing in the area between the buccal side of the alveolar bone surface and the gingival connective tissue.

FIG. 3b is an enlargement of portion b of FIG. 3 showing complete healing in the PDL. Howevers the fibroblasts in the PDL still show a parallel arrangement to the root surface, and the apical portions of the root start to demonstrate root resorption.

DETAILED DESCRIPTION OF THE INVENTION

Figure 1:
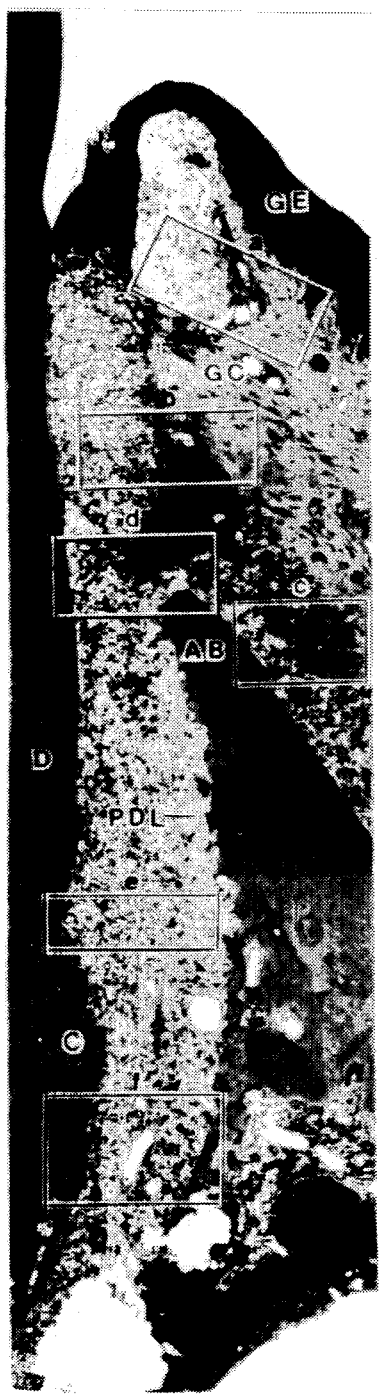
FIG. 1 represents a photomicrograph demonstrating periodontal repair 2 days after reimplantation of a demineralized molar.
Figure 1A:
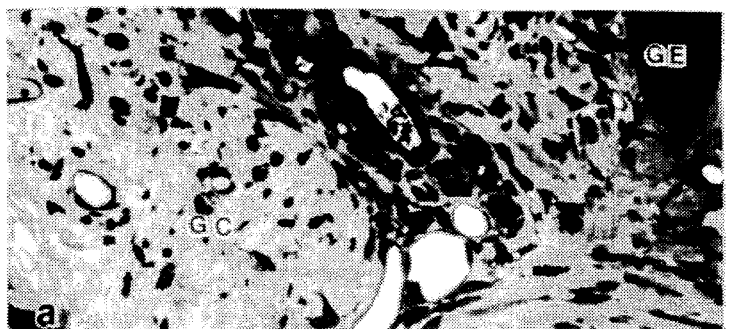
FIG. 1a is an enlargement of portion a of FIG. 1 showing the presence of intact gingival connective tissue.
Figure 1B:
FIG. 1b is an enlargement of portion b of FIG. 1 showing the actively migrating fibroblasts (denoted by arrowhead) toward coagulum from the gingival connective tissue.
Figure 1C:
FIG. 1c is an enlargement of portion c of FIG. 1 showing the actively migrating fibroblasts (denoted by arrowheads) toward the alveolar bone.
Figure 1D:
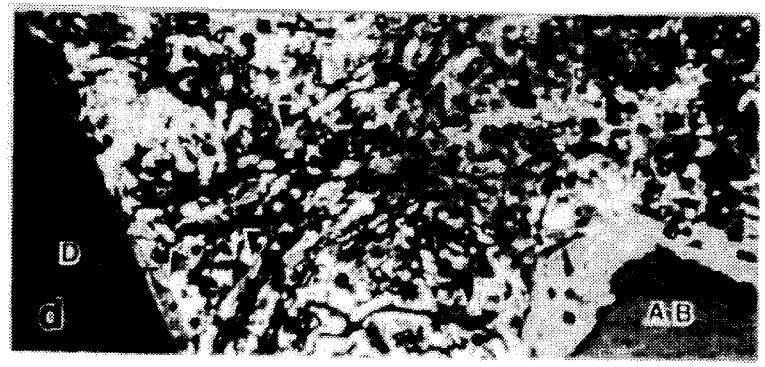
FIG. 1d is an enlargement of portion d of FIG. 1 showing the actively migrating fibroblasts (denoted by arrowheads) toward the root surface.
Figure 1E:
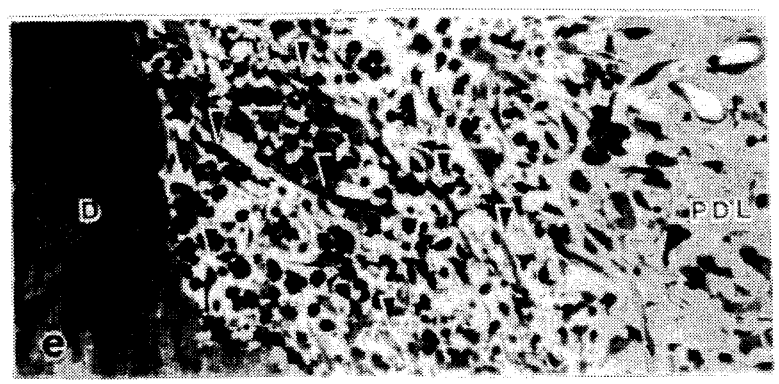
FIG. 1e is an enlargement of portion e of FIG. 1 showing PDL fibroblasts migrate into the wound area.
Figure 1F:
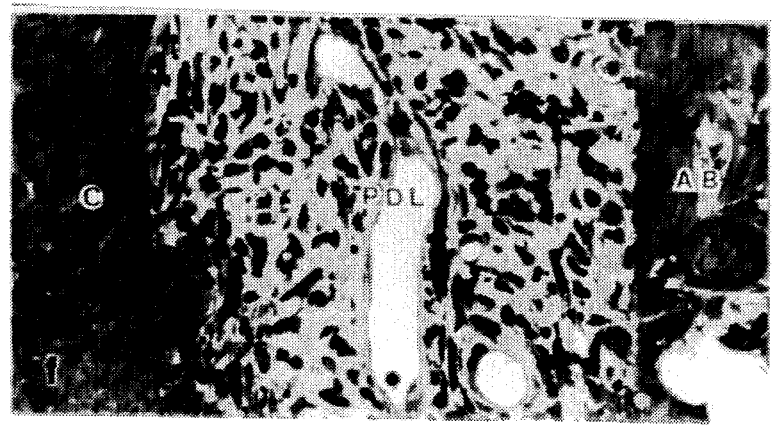
FIG. 1f is an enlargement of portion f of FIG. 1 showing the apical area of PDL which is filled with PDL fibroblasts and collagen fibers.

Considering that the PDL, cementum, and alveolar bone are the products of PDL fibroblasts, cementoblasts, and osteoblasts respectively, and the PDL contains precursor cells for both cementoblasts and osteoblasts, healing of the PDL appears essential for not only the balanced induction of bone and cementum formation, but also successful periodontium regeneration.

It is well known that the exposed root surface as a result of periodontal disease undergoes substantial alterations. These include contamination of the root surface by bacteria and endotoxins, loss of collagen inserted into the root, and possible changes in mineral density and composition of the root surface. This pathologically altered root surface is not only unable to provide the necessary chemotactic stimuli for PDL cells involving in periodontal regeneration, but also unable to serve as an appropriate substrate for attachment of the newly formed collagen fibers to the surface. Since reattachment of the newly formed collagen fibers is essential for the success of periodontal regeneration, the method of the present invention utilizes treatment with a demineralizing agent to effect reattachment of collagen fibers to the root surface. In one embodiment, a preferrable demineralizing agent comprises citric acid.

The treatment of the root surface with citric acid facilitates PDL cell migration toward the root surface and reattachment of new collagen fibers to the root surface. However, this treatment also causes severe root resorption. It has been found that with therapy according to the method of the present invention, connective tissue formation on the root surface and in periodontal wound may be enhanced by application of growth factors directly onto the treated root surface, thereby protecting the root surface from being resorbed.

Growth factors have been proposed for promotion of periodontal regeneration, since growth factors stimulate migration of the precursor cells toward the wound, their proliferation and differentiation. Individual and combinations of various growth factors on PDL cells have been tested in vitro. PDGF isoforms (Matsuda et al., 1992, *J. Periodontol.* 63:515–525; Rutherford et al., 1992, *Archs. Oral Biol.* 37:139–145), insulin-like growth factor-I (IGF-I) (Matsuda et al., 1992, supra) and a combination of PDGF-BB (biologicaly active PDGF existing as homodimer of two chains, beta beta) and dexamethasone (Dex) (Rutherford et al., 1992, *Archs. Oral Biol.* 37:139–145) demonstrated potent mitogenic effect on the cells. Also, PDGF and IGF-I revealed potent chemotactic effects on PDL cells (Matsuda et al., 1992, supra). Furthermore, PDGF-BB showed an enhancing effect on collagen synthesis. Since PDGF-BB has the most potent mitogenic, chemotactic effects on PDL fibroblastic cells and enhanced effect on collagen synthesis; and because PDGF-BB has been shown in the method of the present invention to protect the treated root surface from resorption, a preferred combination in the method of the present invention comprises citric acid and PDGF-BB.

The method of the present invention uses the demineralized root surface as the primary site for the application of growth factors because it was found that: a) citric acid treatment creates more porous spaces on the root surface which are suitable for retention of a larger quantity of the factors applied; and b) the ability of demineralized root surface to retain the growth factor provides a sustained release of growth factors during the early stage of healing (during the several days subsequent to their application to the root surface). It is demonstrated that periodontal regenerative therapy according to the method of the present invention, comprising application of PDGF-BB to the demineralized surface, promotes PDL cell migration from the remaining periodontal ligament coronally along the root surface and results in rapid repopulation of PDL cells. The migrated and repopulated PDL cells, in a cascade-like process, proliferate and differentiate in synthesizing and depositing a cementum matrix of dense connective tissue around the root; new periodontal ligament filling the lesion with connective tissue; and of new alveolar bone. The resulting periodontium in the healed lesion is characteristic in anatomy and architecture of original periodontum, i.e. there is true reattachment of collagen to the root surface, and alveolar bone is anchored to the root surface via a connective tissue attachment (cementum and collagen ligament formation).

A second embodiment of the method of the present invention incorporates into the combination of demineralizing the root surface with application of purified growth factor to the treated root surface, a periodontal barrier membrane such as expanded polytetraflurothylene (PEFE, Gore-Tex Inc.) or resorbable membranes (GUIDOR, J. O. Butler, Inc). The placement of a barrier membrane between the gingiva and the alveolar bone creates a protected space over the defect and induces selective repopulation of PDL fibroblasts in the PDL wound space during initial healing. This also retards the apical migration of the junctional epithelium and the invasion of gingival fibroblasts into the PDL wound space prior to the repopulation of PDL fibroblasts.

Growth factors have been applied to the wound area using carrier molecules such as methylcellulose (Lynch et al., 1989, *J. Clin. Periodontol.* 16:545–548; Lynch et al., 1991, *J. Periodontol.* 62:458–467) or bovine acid insoluble collagen (Rutherford et al., 1992, *J. Periodont. Res.* 27:285–290). Use of carrier molecules to fill the wound space appear to be undesirable with the method of the present invention, since application of a mixture PDGF-BB and carrier molecule has the following disadvantages: a) Since the mixture has to be applied in the wound space, its presence in the wound area will prevent cell migration into the wound space, their proliferation, and deposition of matrix components in the wound. This becomes a serious problem especially when the carrier molecules remain for a long period as the case of insoluble collagen, and will result in delayed wound healing; b) If the removal of carrier molecules requires phagocytic cell involvement, it may develop immunological reactions against the carrier; c) Since the carrier molecules are foreign materials, inflammatory reactions may persist in the wound area until the carrier molecules are completely removed; and d) If the retention time of the carrier in the wound is short, accordingly the growth factor will be available only for a short period, and the growth factor may not deposit on the treated root surface where it has been shown to be effective in initiating the cascade of cellular migration and differentiation resulting in a type of healing characteristic of the architecture and anatomy of the original periodontium.

EXAMPLE 1

Reconditioning/Treatment of the root surface

Although mechanical instrumentation (scaling and root planning) of the contaminated root surface can effectively remove contaminants, it still is unable to promote migration of PDL cells toward the root surface and their attachment to the surface. The presence of a smear layer on the root surface after mechanical instrumentation is believed to be responsible for these unfavorable cell activities and subsequently failure in the establishment of reattachment of newly formed collagen fibers to the root surface. In addition, in the absence of demineralization of the root surface, the newly formed collagen fibers fail to interdigitate with collagen fibrils of the cementum or dentin surface, and eventually detach by artificial splits between the dentin and the layer of new cementum (Nalbandian and Frank, 1980, *J. Periodont. Res.* 15:71–89; Register and Burdick, 1975, *J. Periodontol.* 46:646–655).

Decalcifying agents such as ethylenediamine tetraacetic acid (EDTA), tetracycline and citric acid demineralize the root surface and remove the smear layer from the denuded root surface. However, EDTA treatment apparently changes the morphology of exposed collagen fibrils (Lasho et al., 1982, *J. Periodontol.* 54: 210–220). Due to this undesirable effect of EDTA on collagen structure and its well known inhibitory effects on various cellular activities, EDTA has not been used in the method of the present invention as a demineralizing agent. Tetracycline HCl has showed conflicting outcomes when used as a demineralizing agent. Wikesjo et al., (1988, *J. Clin. Periodontol.* 15:73–80) reported that tetracycline demonstrates an equivalent ability, as compared to citric acid, to induce cell migration as well as reattachment of collagen fibers to the root surface. On the other hand, Claffey et al., (1987, *Acta Odontol. Scand.* 45:141–146) found that citric acid showed better attachment gain than that achieved using tetracycline. In addition, demineralization of the root surface with tetracycline HCl seems to be achieved by HCl, but not by tetracycline itself. Therefore, although tetracycline HCl may be useful as a demineralizing agent in the method of the present invention, the preferred embodiment uses citric acid as the demineralizing agent.

Since reattachment of the newly formed collagen fibers is essential for the success of periodontal regeneration, the effect of citric acid treatment on the reattachment of collagen fibers to the root surface was investigated using the rat reimplantation model. This model was developed in our laboratory and found to be very useful to examine the effects of various potentially useful modifiers in periodontal regenerative therapy.

Reconditioned rat maxillary molars were prepared as follows. Male Sprague-Dawley rats (110±5 gm body weight) were fed powdered rat chow containing 0.4% β-aminopropionitrile (β-APN) for five days to reduce the tensile strength of collagen molecules. This treatment permits gentle extraction of the first maxillary molars with minimum damage to the surrounding periodontal tissues. Under anesthesia with Nembutal (5mg/100 gm body weight), the first maxillary molars were extracted using forceps, washed in sterile distilled water overnight at 4° C. The teeth were then treated with bacterial collagenase (200 μg/ml of 0.02 Tris-HCl, pH 7.4 containing 0.2M NaCl and 50 mM $CaCl_2$) for 3 hours at 37° C. to digest PDL collagen fibers on the root surface. After washing in sterile water overnight at 4° C., the mesial root surface was demineralized by application of citric acid for 1 minute. The teeth were then washed in sterile distilled water for 30 minutes, dehydrated briefly in 90% ethanol, and air dried.

Citric acid-treated or untreated molars were implanted as follows. Under anesthesia with Nembutal, two corresponding first maxillary molars were extracted from each rat. After the bleeding was controlled, two citric acid-treated or untreated molars were implanted. Under the conditions of this experiment and using highly inbred isogeneic rats, immunologic acceptance occurs.

To observe the effect of citric acid treatment on the reatttachment of newly formed collagen fibrils to the root surface, tissue preparation of the implants was prepared as follows. Four rats with 8 reimplanted molars (2 molars/rat) were sacrificed at 2, 4, 6, and 8 days after reimplantation of teeth by intracardiac perfusion with 2.5% glutaraldehyde in 0.1 M sodium cacodylate buffer, pH 7.4. The first maxillary molar and the surrounding periodontal tissues were cut mesiodistally through the midline, processed and embedded in Epon mixture as previously described (Cho and Garant, 1981, *Anal. Rec.* 199: 309– 320).

Figure 2:
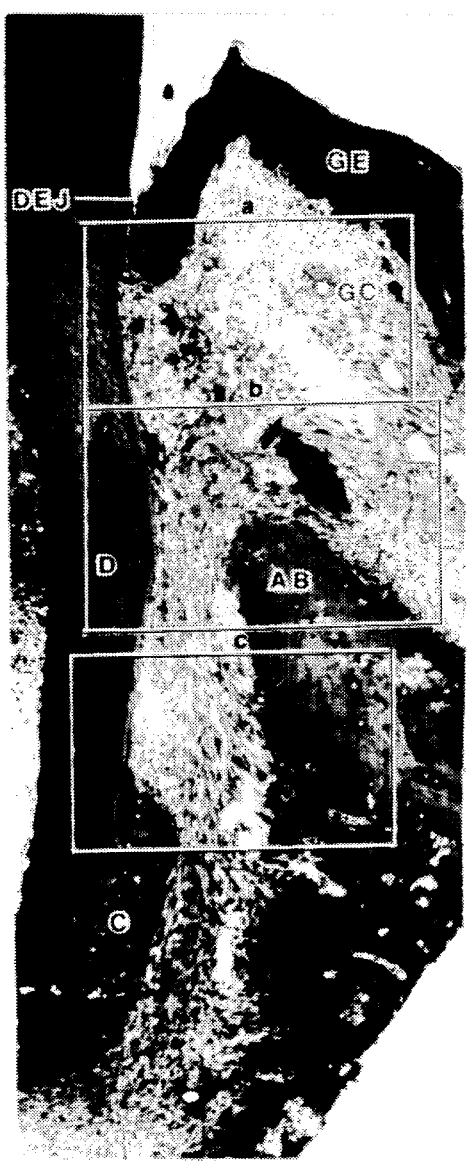
FIG. 2 represents a photomicrograph revealing periodontal repair 4 days after reimplantation of a demineralized molar.
Figure 2A:
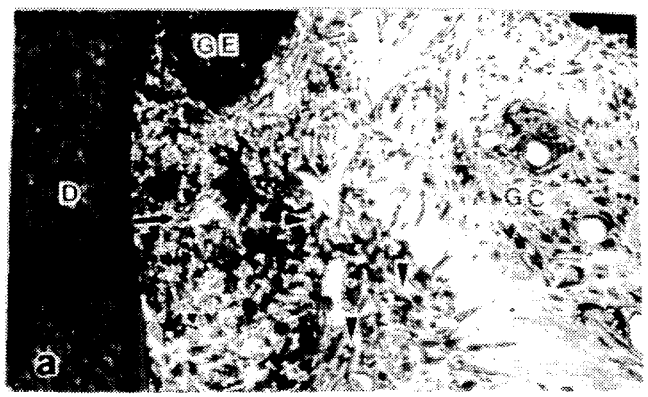
FIG. 2a is an enlargement of portion a of FIG. 2 showing that the cervical area still contains coagulum and is the site with the least progress in wound healing.
Figure 2B:
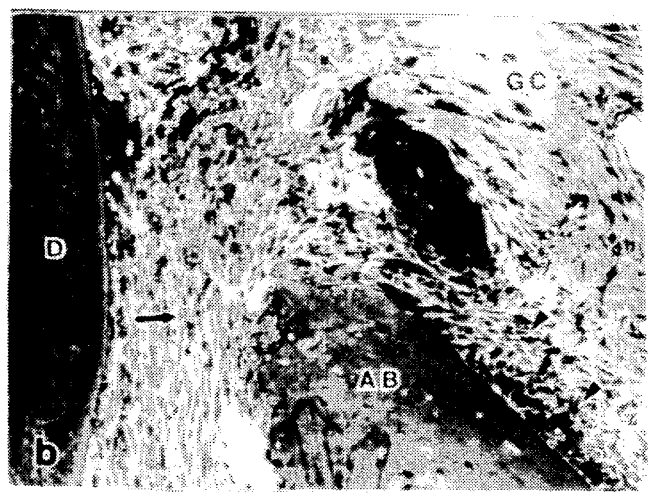
FIG. 2b is an enlargement of portion b of FIG. 2 showing many fibroblasts in the wound area between the buccal side of the alveolar bone and the gingival connective tissue.
Figure 2C:
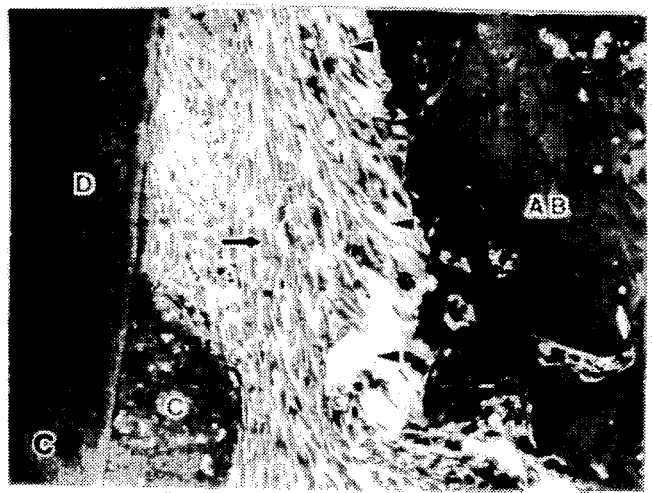
FIG. 2c is an enlargement of portion c of FIG. 2 showing numerous fibroblasts and newly formed collagen fibers in the wound area of the PDL.
Figure 4:
FIG. 4 represents a photomicrograph demonstrating periodontal regeneration 8 days after reimplantation of an undemineralized molar.
Figure 4A:
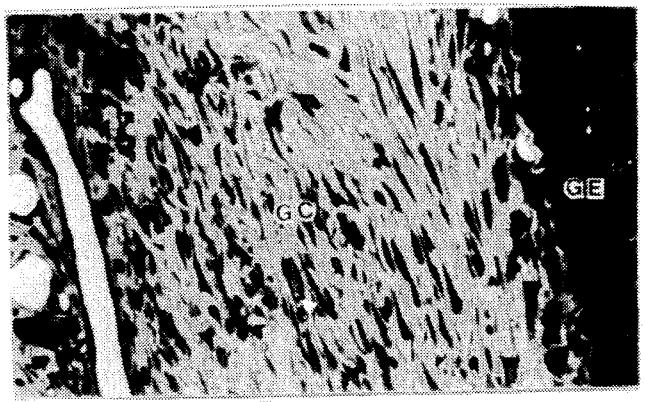
FIG. 4a is an enlargement of portion a of FIG. 4 showing complete healing in the gingival connective tissue; however note the artificial split (arrowheads) between the root surface and the connective tissue is prominent.
Figure 4B:
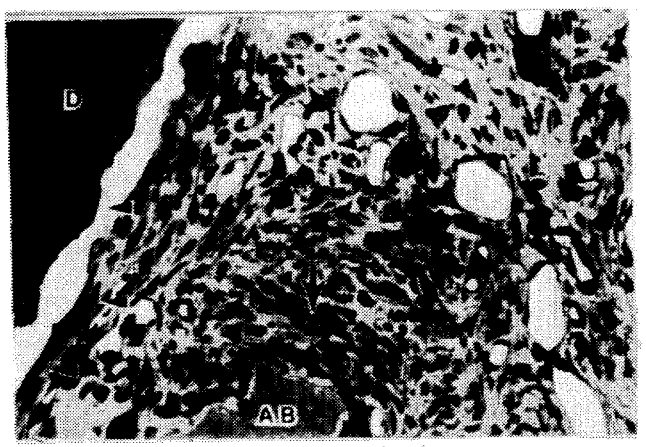
FIG. 4b is an enlargement of portion b of FIG. 4 showing complete healing in the gingival connective tissue; however note the artificial split (arrowheads) between the root surface and the connective tissue is prominent.
Figure 4C:
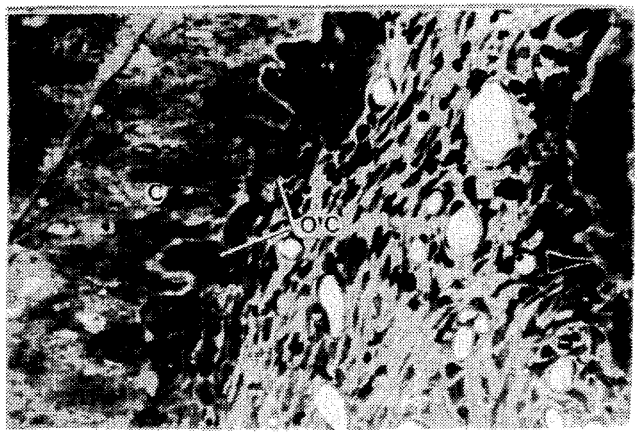
FIG. 4c is an enlargement of portion c of FIG. 4 showing complete healing in the PDL; however note the artificial split (arrowheads) between the root surface and the connective tissue is prominent.

Periodontal wound spaces subjected to the present studies on healing and regeneration of the periodontium were created as the result of extraction and reimplantation of the first maxillary molars. At one or two days after reimplantation, the space was filled primarily with plasma rich in fibrin and infiltrated inflammatory cells. In spite of tissue trauma in the PDL and gingival connective tissue, the gingival fibroblasts as well as PDL fibroblasts in the vicinity of the wounds remained viable and able to participate in wound healing. At 2 days, the PDL fibroblasts and gingival fibroblasts adjacent to the wound space began to migrate toward the wound space (FIGS. 1a, 1b, 1c, and 1d). At 4 days, numerous PDL fibroblasts appeared to deposit collagen matrix during their migration toward the cervical area and filled the apical wound area (FIGS. 2a, 2b, and 2c). However, the fibroblasts and the newly formed PDL collagen fibers demonstrated a parallel orientation to the root surface (FIGS. 2b and 2c) rather than vertical or oblique orientation observed in the normal PDL. At 6 days, cementoclasts started to appear over the cementum and are involved in resorption of the cementum (FIGS. 3a and 3b). However, citric acid treatment was always accompanied by severe root resorption in the later stage of periodontal regeneration. At 8 days, the wound space demonstrated relatively complete healing including formation of the junctional epithelium on the enamel surface (FIG. 4)(no downgrowth was observed beyond the cementoenamel junction (CEJ)), the PDL (FIG. 4c) and the gingival connective tissue (FIGS. 4a and 4b). However, an artificial split between the root surface and the connective tissue is prominent (FIGS. 4, 4a, and 4b). In contrast, demineralization of the root surface by topical treatment with citric acid and growth factor in accordance with the method of the present invention facilitated the reattachment of the newly formed PDL collagen fibers to the root surface, and prevented an artificial split between the root surface and PDL collagen FIG. 5).

EXAMPLE 2

Effects of treatment of the root surface with a combination of citric acid and PDGF-BB on resorption of the root surface Rats were fed a powdered diet containing 0.45% β-APN for five days. The first maxillary molars were extracted, treated with bacterial collagenase, and demineralized by citric acid as described previously. The root surface was then treated with PDGF-BB (1 μg/ml) and reimplanted. Two rats each (with four reimplanted molars) were sacrificed at 1, 2, 4, and 6, days after reimplantation. The molars were processed for light microscopy analysis as described previously.

Treatment with PDGF-BB significantly improved the overall healing and regeneration of the periodontal tissues. At 6 days after reimplantation, the PDL showed complete healing including repopulation of PDL fibroblasts and deposition of functional collagen fibers (FIGS. 5a, 5b, and 5c). The newly formed collagen fibers demonstrated not only an oblique orientation, but also reattachment to the root surface. Most importantly, no root resorption or ankylosis was observed at 6 days and thereafter. Thus, it is shown by these experiments that the method according to the present invention, i.e. treatment of the demineralized root surface with PDGF-BB, enhances PDL cell migration toward the root surface, PDL cell repopulation, and formation of PDL collagen fibers by the cells. In particular, the accelerated cell migration toward the surface is coupled with rapid deposition of collagen, formation of Sharpy's fibers and subsequently reattachment of the collagen. Also, the facilitated establishment of reattachment of collagen fibers to the demineralized root surface appeared to protect the root surface from being resorbed.

EXAMPLE 3

Capacity of the demineralized root surface to retain and to provide sustained release of growth factor applied thereto To investigate if the demineralized root surface has the ability of retention and sustained release of growth factors applied, the release and retained $^{125}$I-EGF (epidermal growth factor) was studied radioautographically using the rat reimplantation method.

The first maxillary molars were extracted, treated with bacterial collagenase, demineralized with citric acid, washed in sterile distilled water, and air dried as described above. To determine the capacity of demineralized root surface to retain and release EGF after its application to the root surface, mouse EGF was radioiodinated by the chloramine-T technique. One µl of $^{125}$I-EGF (Specific activity: approximately 100 µCi/µg) containing 5 µCi was then evenly applied to the mesial root surface and reimplanted as described previously. Three rats each (a total of 6 teeth) were sacrificed at 1 hour or 1,2,4, 6, and 8 days after reimplantation by intracardiac perfusion with 2.5% glutaraldehyde in 0.1M sodium cacodylate buffer, pH 7.2. The first maxillary molars with the surrounding periodontium were cut mesiodistally, and embedded in Epon as described above. For light microscopic radioautography, three or four 1.5 µm sections from each block were mounted on glass slidess coated with Kodak NTB-2 liquid emulsion, exposed for 23 days at 4° C., developed under identical conditions, and stained with 1% toluidine blue in sodium veronal acetate buffer.

The radioautographs obtained at different time periods after reimplantation of the $^{125}$I-EGF-treated molars demonstrated the presence of silver grains at different density on the root surface (cementum). The number of silver grains was highest at 1 hour (FIGS. 6, 6a, 6b and 6c) and decreased gradually thereafter. However, even at 8 days after reimplantation, a small number of silver grains still remained on the root surface (FIGS. 7, 7a, 7b, and 7c). These results demonstrate that the demineralized root surface has a capacity to retain applied growth factors and provide a sustained release of growth factors during the first week or more after their application to the root surface. The phenomenon of sustained release of the applied factor from the root surface may enhance chemotaxis of PDL fibroblasts to the root surface and stimulate their proliferation at the early stage of periodontal healing, contributing to rapid repopulation of PDL fibroblasts and repair of the PDL.

The citric acid can be incorporated into a composition also comprising a vehicle such as gel with adherent and viscous properties, wherein the vehicle would enhance the binding and retention time of the citric acid to the root surface. Alternatively, the composition can comprise a vehicle containing both citric acid and PDGF-BB as active ingredients since PDGF-BB is active at low pH such as that of citric acid.

EXAMPLE 4

Periodontal regeneration of Class III furcation lesions

The method of the present invention comprising the combination of applying PDGF-BB directly to demineralized root surface, and use of a periodontal barrier membrane, was compared to the use of a demineralized root surface and a barrier membrane without growth factor for the ability to induce periodontal healing and regeneration of furcation defects created in beagle dogs.

A total of 6 male beagle dogs (2–3 years old) without any general or oral health problems were used. Three weeks prior to surgery, the first and third mandibular premolars were extracted and the crown of the first molars were amputated at the level of the surgically reduced alveolar crest under general anesthesia with IV injection of Pentobarbital Sodium (25–30 mg/kg). The second and fourth mandibular premolars (p2 and p4) received presurgical treatment including scaling and root planning. The teeth were brushed daily with a brush dipped in 0.5% Chlorhexidine Gluconate.

For creation of horizontal furcation defects (Class III), the animals were injected preoperatively with atrophine sulfate to reduce salivation and then anesthetized with intravenous Pentobarbital and Lidocaine HCl. After elevation of muco periosteal flaps following intrasulcular and crestal incisions, horizontal furcation defects were created around the mandibular p2 and p4 according to the procedures of Klinge et al. (1985, *J. Clin. Periodontol.* 12:369–373) and Wikesjo et al. (1988, supra). The size of the induced defects for the p2 and p4 measures from the CEF to the marginal bone over the mesial and distal roots were approximately 3.5 and 4.5 mm, respectively. Orthodontic ligature wires were placed around the CEJ and the wounds were closed by suturing the flaps over the reduced alveolar bone. During a 4-week postoperative period, the surgically denuded roots were exposed to the oral environment to allow the growth of dental plaque and to induce chronic periodontal disease on the surface. At 4 weeks after creation of the defects, the ligature wires were removed from the teeth, and they were cleaned using and ultrasonic scaler and polished with pumice. For plaque control until reconstructive surgery, daily brushing with 2% Clorhexidine Gluconate was performed.

To evaluate the effects of PDGF-BB, and a combination of PDGF-BB and a barrier membrane on periodontal regeneration, reconstructive surgery was performed 1 week after the initial therapy. After elevation of mucoperiosteal flaps, the teeth were isolated with gauze and all granulation tissue was removed and the root surfaces were thoroughly debrided with curettes, and received one of the following treatments. Two dogs (4 teeth) each were used for each time period. The root surfaces of the right mandibular premolars were conditioned with saturated citric acid (pH1) by topical application to the exposed tooth surface for 3 minutes using small cotton balls. The surfaces were washed thoroughly by irrigation with sterile water. After air drying, the surfaces of the left teeth were treated with a vehicle only. After treatment of the root surface, a PTFE membrane was circumferentially placed around the tooth surface coronal to the alveolar crest according to the manufacturer's direction. The membrane was retained at the level of the CEJ, and secured with interrupted sutures.

The horizontal furcation defects were also treated according to the method of the present invention. Demineralized root surface of the left mandibular premolars were treated with recombinant human (rh) PDGF-BB (5 µg/10 µl in 0.01M acetic acid/tooth) using a micropipette. The membranes were placed around the teeth as described above.

Following either treatment, the mucoperiosteal flaps were elongated by periosteal fenestration and sutured with interrupted silk in a coronal position that provides initial coverage of all but the cusp tips of the teeth. The wounds were protected by feeding the dogs with a soft diet during the first four post-surgical weeks and then a hard diet for the remaining period of study. To ensure optimal healing, plaque control were maintained postsurgically by: a) daily irrigation with 2% Clorhexidine Gluconate throughout the experiment; and b) systemic antibiotic treatment with Penicillin G bezathine administered IM for two weeks. Two weeks after surgery, sutures were removed.

At 5, 8 and 11 weeks after reconstructive surgery, two animals each were anesthetized by IV injection of Nembutal. After the carotid arteries and jugular veins are exposed, the animals were perfused with 2.6% glutaraldehyde in 0.1 phosphate buffer through the carotid arteries according to the procedures of Cho et al. (1987, *J. Periodontol. Res.* 22:313–319). The premolars with the surrounding periodontal tissues were further fixed in Karnovsky's fixative, cut mesiodistally (2-mm thick slices) using a thin sectioning machine equipped with a diamond wheel, and decalcified in EDTA containing 3% glutaraldehyde. The tissue slices were then post-fixed in 1% $OsO_4$, prestained in 1% uranyl acetate in 0.1M maleate buffer, dehydrated, and embedded in Epon as described previously. One-μm thick sections were cut on a microtome, placed on gelatin-coated glass slides, and stained with Toluidine blue.

One most centrally located block was selected and subjected to histometric analysis for each tooth. One-um thick sections were cut and stained with 1% toluidine blue. A montage for each block was prepared after taking photographs in a magnification of 20× and printing at a final magnification of 100×, and subjected to histometric analysis using a Knotton MOP analyzer. For morphometric analysis, the following areas were measured: 1) the total defect area-the defect area created by surgery which is lined by the mesial and distal root surface, the furcation fornix and the horizontal bone defect surface; 2) the unoccupied area-empty space; 3) the epithelium- the area occupied by epithelial cells; 4) inflamed tissue- a loose connective tissue infiltrated with numerous inflammatory cells; 5) new connective tissue- the area of newly formed dense connective tissue with many fibroblasts, but devoid of inflammatory cells; 6) new bone; and 7) new PDL. Statistical analysis was performed using paired t-test to determine differences between groups. The test of significance was performed at the 95% confidence interval compared to control.

Periodontal healing and regeneration after therapy with citric acid demineralization and insertion of a barrier membrane was compared with healing and regeneration after therapy according to the method of the present invention using histometric analysis of the furcation defects. For this purpose, the areas occupied by epithelium, inflamed tissue, and newly formed connective tissue, bone and periodontal ligament during healing of the defects were measured and compared by statistical analysis, and the data is summarized in Table 1 (Guided tissue regeneration (GTR); PDGP modulated GTR (PGTR)). In general, the furcation defect area at the early stage of healing was characterized by the presence of the unoccupied area, epithelium and inflamed tissue. However, as healing progresses, these areas were gradually replaced by the newly formed dense connective tissue, the PDL and alveolar bone. The data from histometric analysis demonstrated that the periodontal healing and regeneration after therapy according to the method of the present invention progressed faster and more effectively when compared to the results after therapy comprising just demineralization and insertion of a barrier membrane.

TABLE 1

| | Measurements within the Furcation Lesion | | | | | |
|---|---|---|---|---|---|---|
| | 5 weeks | | 8 weeks | | 11 weeks | |
| | GTR | PGTR | GTR | PGTR | GTR | PGTR |
| Epithelium & unoccupied area | 8.6 (±14.5) | 7.0 (±14.0) | 26.3* (±10.8) | 0 (±0) | 4.3 (±7.1) | 0 (±0) |
| Inflammed Tissue | 39.1 (±30.7) | 37.3 (±18.3) | 31.3* (±6.2) | 0 (±0) | 9.4 (±6.6) | 0 (±0) |
| New Connective Tissue | 37.7 (±25.2) | 27.0 (±12.0) | 23.3 (±8.1) | 0 (±0) | 12.0 (±10.9) | 0 (±0) |
| Newly formed Bone | 10.6 (±15.2) | 21.6 (±24.1) | 14.6* (±9.5) | 80.0 (±6.3) | 60.4♦ (±16.0) | 87.2 (±3.5) |
| Periodontal Ligament | 4.1 (±2.4) | 7.1 (±7.6) | 4.6* (±1.2) | 20.5 (±2.4) | 14.0 (±3.8) | 13.3 (±2.9) |

GTR: Guided tissue regeneration
PGTR: PDGF-modulated GTR
Mean (%)
(±S.D)?
n = 4, except 8 weeks M group (n = 3)
*: p < 0.01
♦: p < 0.05

As shown in Table 1, healing of Class III furcation lesions, which are "through-and-through", was enhanced after therapy with demineralization and insertion of a barrier membrane. However, when therapy was performed according to the method of the present invention, there is a statistically significant greater amount of PDL formed at 8 weeks and bone formed at 8 and 11 weeks in the lesion. Also with therapy according to the method of the present invention, at 8 weeks there is less epithelium and unoccupied area, less inflamed tissue, and less connective tissue. A significant amount of epithelium and inflammation are undesirable elements in healing of the furcation. A healed furcation would be fully filled with newly formed bone and PDL. The newly formed bone fills 80% of the lesion at 8 weeks, and 87% of the lesion at 11 weeks with therapy according to the method of the present invention, as compared to 14.6% of the lesion at 8 weeks, and 60% at 11 weeks with therapy comprising just demineralization and insertion of a barrier membrane.

Figure 5:
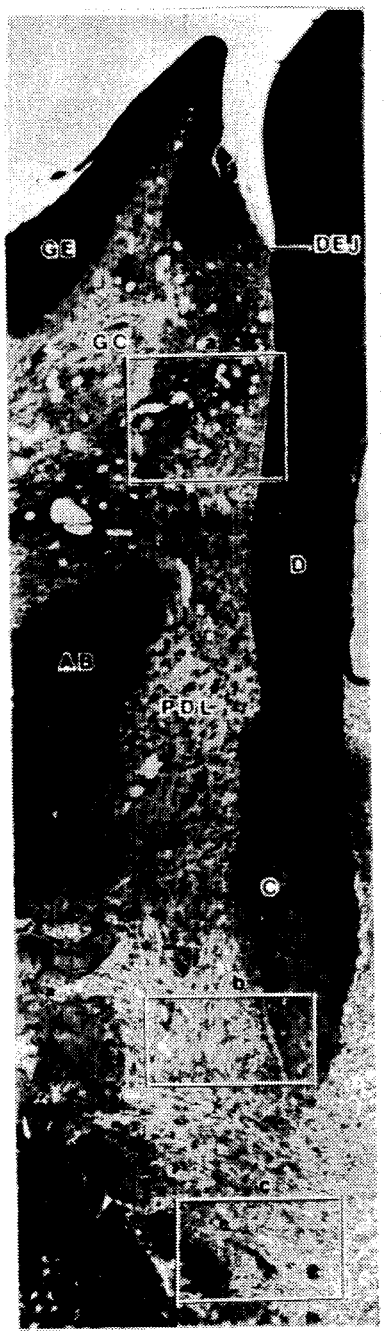
FIG. 5 represents a photomicrograph showing good overall periodontal regeneration 6 days after reimplantation according to the method of the present invention.
Figure 5A:
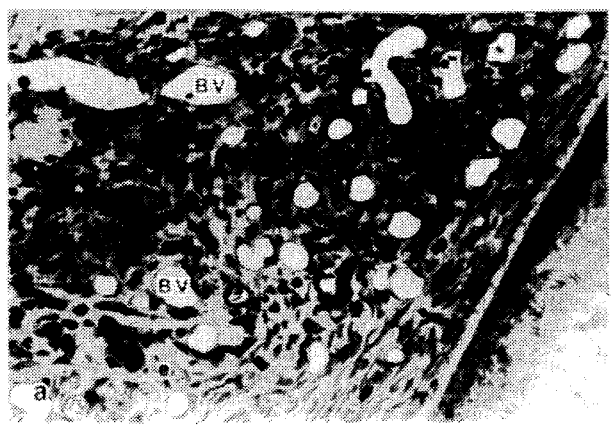
FIG. 5a is an enlargement of portion a of FIG. 5 showing the apical wound area is in the process of healing.
Figure 5B:
FIG. 5b is an enlargement of portion b of FIG. 5 showing well organized and fully regenerated PDL which consists of numerous collagen fibers and fibroblasts with an oblique orientation to the root surface.
Figure 5C:
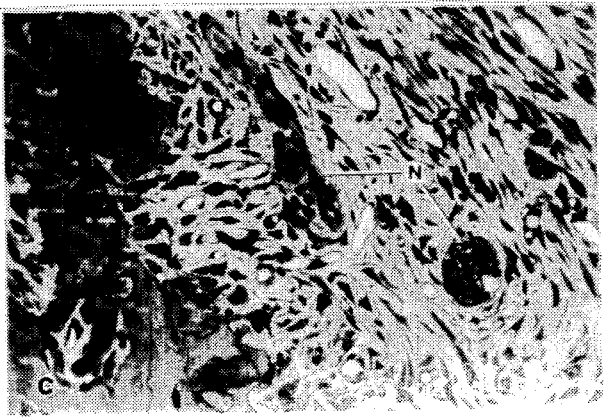
FIG. 5c is an enlargement of portion c of FIG. 5 showing well organized and fully regenerated PDL which consists of numerous collagen fibers and fibroblasts with an oblique orientation to the root surface.
Figure 6:
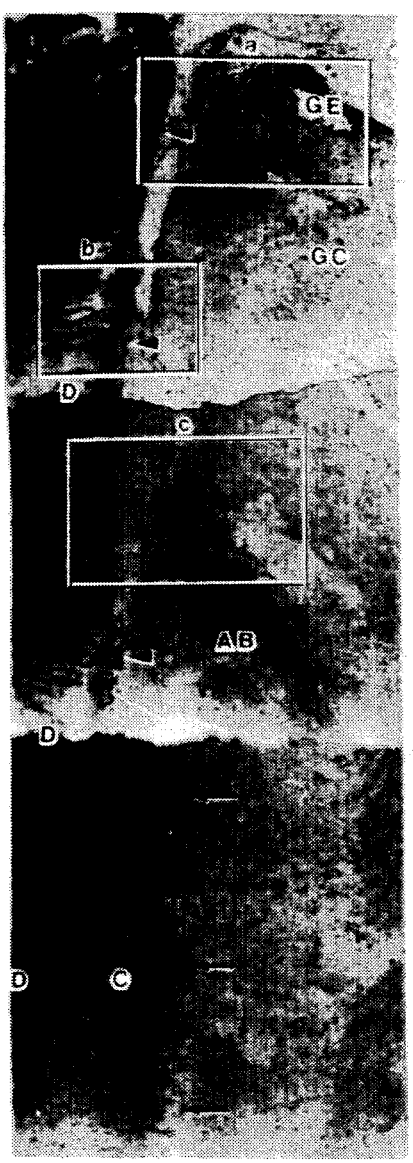
FIG. 6 represents a radioautograph showing localization of epidermal growth factor (EGF) during periodontal healing at 1 hour after reimplantation of an $^{125}$I-EGF-treated molar.
Figure 6A:
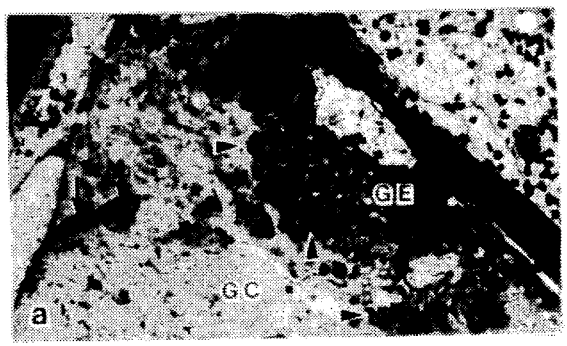
FIG. 6a is an enlargement of portion a of FIG. 6 showing heavy labeling over gingival epithelium.
Figure 6B:
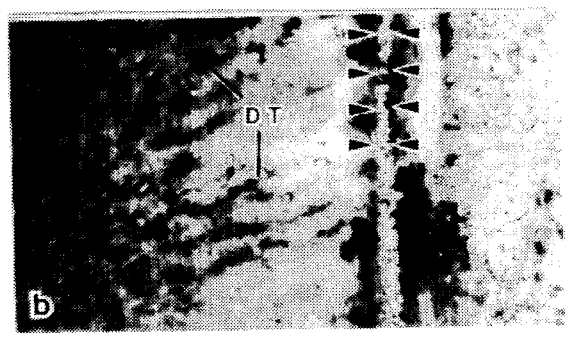
FIG. 6b is an enlargement of portion b of FIG. 6 showing heavy labeling over dentinal tubules, and over acellular extrinsic fiber cementum (the areas between the arrowheads).
Figure 6D:
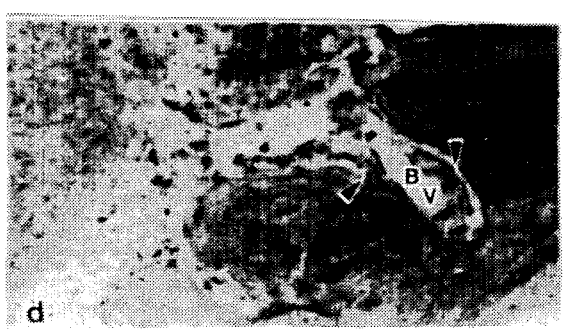
FIG. 6d is an enlargement of portion d of FIG. 6 showing a small number of grains around the blood vessel.
Figure 6C:
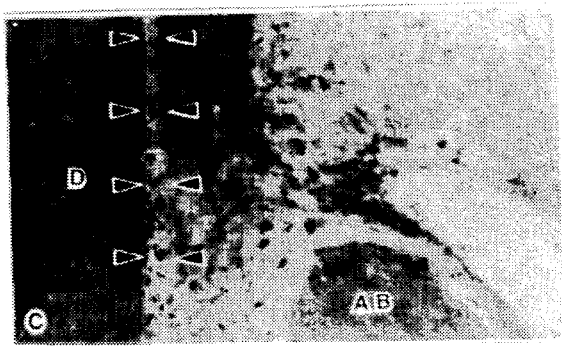
FIG. 6c is an enlargement of portion c of FIG. 6 showing heavy labeling over acellular extrinsic fiber cementum (the areas between the arrowheads).
Figure 7:
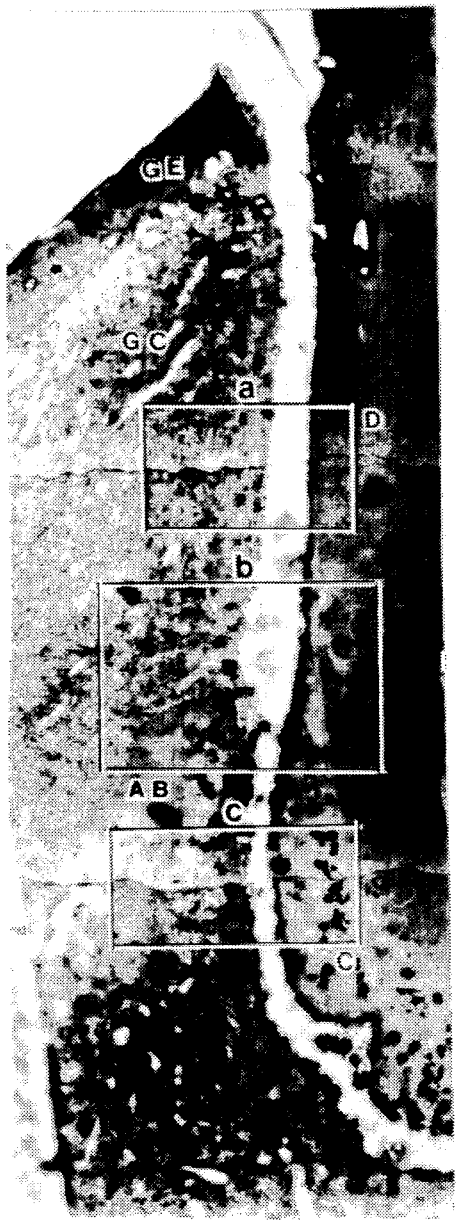
FIG. 7 represents an radioautograph after reimplantation of an $^{125}$-I-EGF-treated molar.
Figure 7A:
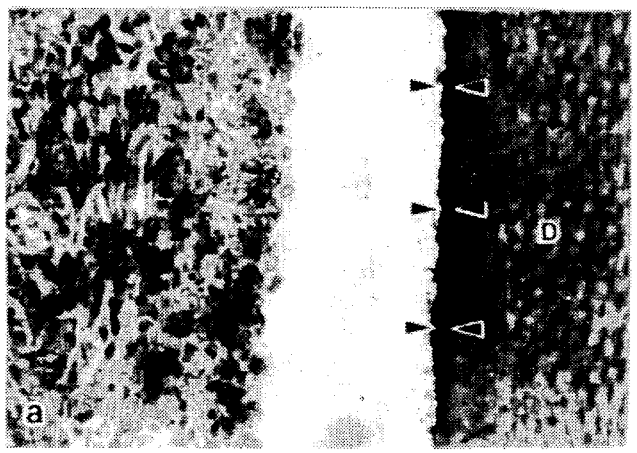
FIG. 7a is an enlargement of portion a of FIG. 7 demonstrating the presence of a small amount of labeling over acellular extrinsic fiber cementum (the areas between the arrowheads).
Figure 7B:
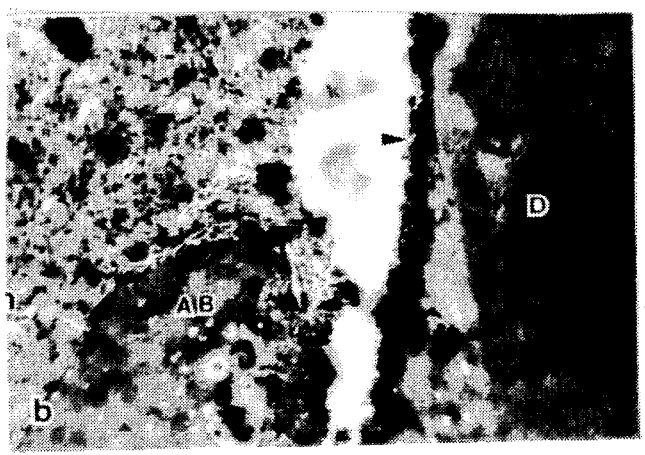
FIG. 7b is an enlargement of portion b of FIG. 7 demonstrating the presence of a small amount of labeling over acellular extrinsic fiber cementum (the areas between the arrowheads).
Figure 7C:
FIG. 7c is an enlargement of portion c of FIG. 7 demonstrating the presence of a small amount of labeling over cellular mixed stratified cementum (denoted by the arrowheads).

As indicated by the healing of furcation defects, and by the photomicrographs of FIG. 5, guided tissue regenerative therapy according to the method of the present invention (i.e. application of PDGF-BB directly to the demineralized root surface) induced an orderly cascade comprising PDL cell migration from the remaining PDL coronally along the root surface and rapid repopulation of PDL cells. Subsequently synthesis and deposition of dense connective tissue by the repopulated PDL cells occurs around the root as well as in the wound space thereby filling the lesion with connective tissue. Remodeling of the newly formed connective tissue then takes place during periodontal regeneration. The healed furcation shows regenerated tissue characteristic of the architecture and anatomy of the original periodontium, i.e. newly formed cementum; periodontal ligament; and alveolar bone, wherein the root surface is anchored to the bone via a connective tissue attachment.

It should be understood that while the invention has been described in detail herein, the examples were for illustrative purposes only. Other modifications of the embodiments of the present invention that are obvious to those skilled in the art of soft tissue and bone regeneration, and related disciplines, are intended to be within the scope of the appended claims.

We claim:

1. A method for inducing periodontal regeneration in a wound of a mammal with periodontal disease or other condition requiring periodontal regeneration, said method induces soft tissue, cementum and alveolar bone healing of a type characteristic of the anatomy and architecture of undiseased periodontium, comprising the steps of:
   a) treating the root surface in the wound with mechanical instrumentation and a composition comprising a demineralizing agent;
   b) applying a therapeutically effective amount of a growth factor directly to the treated root surface, wherein said growth factor is one or more factors selected from the group consisting of platelet-derived growth factor in a form having two beta chain (PDGF-BB), platelet-derived growth factor in a form having an alpha and a beta chain (PDGF-AB) and IGF-I;
   c) inserting a periodontal barrier, wherein the barrier is positioned between the gingival tissue and the root surface treated according to steps. a) and b) to create and maintain a space for regeneration, and wherein the barrier is selected the group consisting of a membrane, a biodegradable polymer, and a biocompatible porous material; and
   d) closing the wound to allow for regeneration.

2. The method of claim 1, wherein the composition further comprises a vehicle, such as a gel, with adherent and viscohs properties to enhance the binding, retention time, and activity of the demineralizing agent to the root surface.

3. The method of claim 2, wherein the composition further comprises a therapeutically effective amount of a growth factor thereby obviating the need to apply the growth factor in a separate step of the method, said vehicle also enhances the binding, retention time, and activity of the growth factor.

4. The method of claim 1, wherein the demineralizing agent comprises citric acid.

5. The method of claim 1, wherein the growth factor is PDGF-BB.

6. The method of claim 1, wherein the wound consists of Class III furcation lesions or other periodontal tissue defects which result from periodontal disease, or other destructive or traumatic process to the periodontal tissue.

7. A method for inducing regeneration in a wound site comprising damaged bone, periodontium, connective tissue, or ligament of a mammal, said method induces soft tissue and bone regeneration resulting in soft tissue, cementum and bone characteristic of the anatomy and architecture of undamaged tissue in the regeneration site of the mammal, comprising the steps of:
   a) treating damaged root surface in the wound site with mechanical instrumentation and a composition comprising a demineralizing agent;
   b) applying a therapeutically effective amount of a growth factor directly to the treated root surface, wherein said growth factor is one or more factors selected from the group consisting of platelet-derived growth factor in a form having two beta chain (PDGF-BB), platelet-derived growth factor in a form having an alpha and a beta chain (PDGF-AB) and IGF-I;
   c) inserting a barrier, wherein the barrier is positioned between the surrounding tissue of the wound site and the root surface treated according to steps a) and b) to create and maintain a space for regeneration, and wherein the barrier is selected the group consisting of a membrane, a biodegradable polymer, and a biocompatible porous material; and
   d) closing the wound to allow for regeneration.

8. The method of claim 7, wherein the composition further comprises a vehicle, such as a gel, with adherent and viscous properties to enhance the binding and retention time of the demineralizing agent to the root surface.

9. The method of claim 8, wherein the composition further comprises a therapeutically effective amount of a growth factor thereby obviating the need to apply the growth factor in a separate step of the method.

10. The method of claim 7, wherein the demineralizing agent comprises citric acid.

11. The method of claim 7, wherein the growth factor is PDGF-BB.

* * * * *